United States Patent [19]

Bakalyar et al.

[11] 4,182,184
[45] Jan. 8, 1980

[54] SAMPLE INJECTOR

[75] Inventors: Stephen R. Bakalyar, Berkeley; Reginald E. Sylvester, Hercules, both of Calif.

[73] Assignee: Rheodyne Incorporated, Berkeley, Calif.

[21] Appl. No.: 969,331

[22] Filed: Dec. 14, 1978

[51] Int. Cl.² ............................................. G01N 1/10
[52] U.S. Cl. ............................................... 73/422 GC
[58] Field of Search ................................... 73/422 GC

[56] References Cited

U.S. PATENT DOCUMENTS

| | | | |
|---|---|---|---|
| 3,916,692 | 11/1975 | Abrahams et al. | 73/422 GC |
| 3,961,534 | 6/1976 | Gundlefinger | 73/422 GC |
| 4,022,065 | 5/1977 | Rain et al. | 73/422 GC |
| 4,068,528 | 1/1978 | Gundlefinger | 73/422 GC |

*Primary Examiner*—S. Clement Swisher
*Attorney, Agent, or Firm*—Freilich, Hornbaker, Wasserman, Rosen & Fernandez

[57] ABSTRACT

A sample injector is described for receiving a sample at atmospheric pressure and injecting it at a high pressure into a chromatographic column, which is convenient to use and which avoids loss of the sample. The device includes a rotor and stator with flat adjacent faces, and a passage in the rotor for receiving a syringe needle that can transfer the sample into an aligned port in the stator, wherein the needle-receiving passage extends parallel to the axis of rotation of the rotor but is offset therefrom. This enables the needle to be inserted with its tip flush with the interface between the rotor and stator, so that no sample lies in the rotor passage after operation of the syringe, and so that rotation of the rotor isolates the syringe needle from the high pressure ports. With this arrangement, and with the needle end ground perpendicular to its axis, all of the sample in the syringe is transferred to the stator port and from there to the column.

23 Claims, 15 Drawing Figures

LOAD

LOAD

INJECT

INJECT

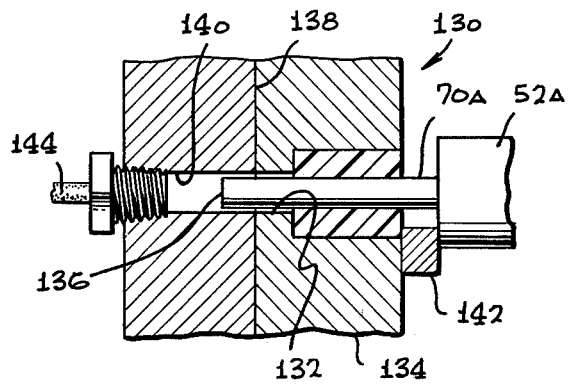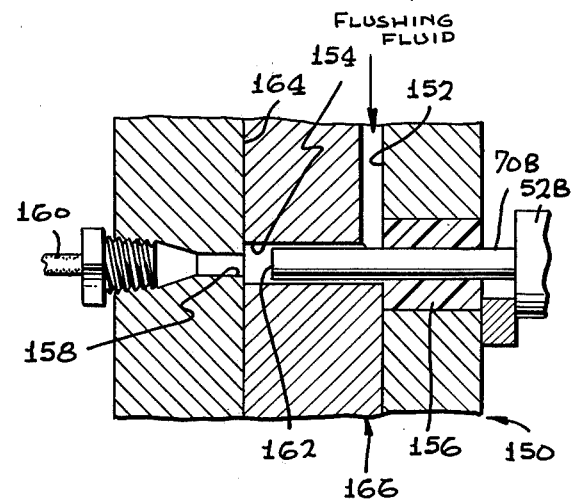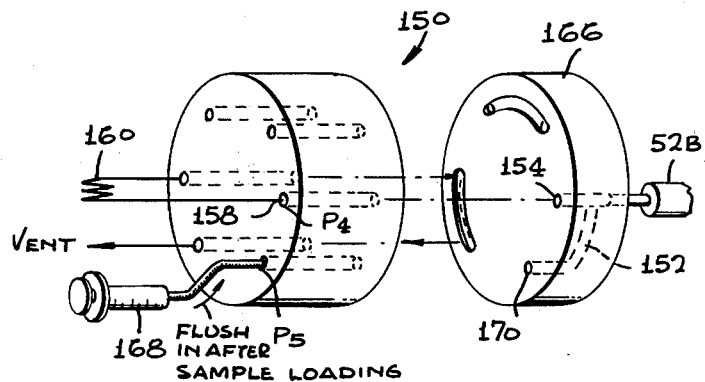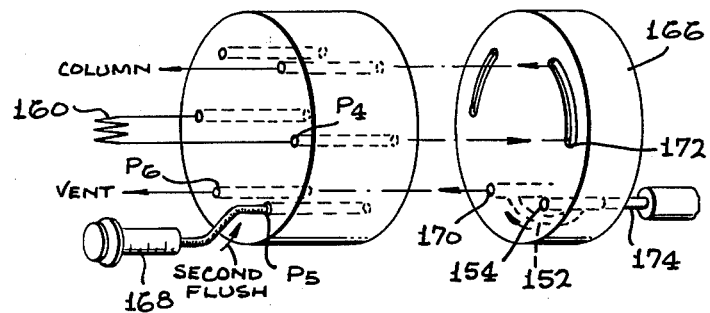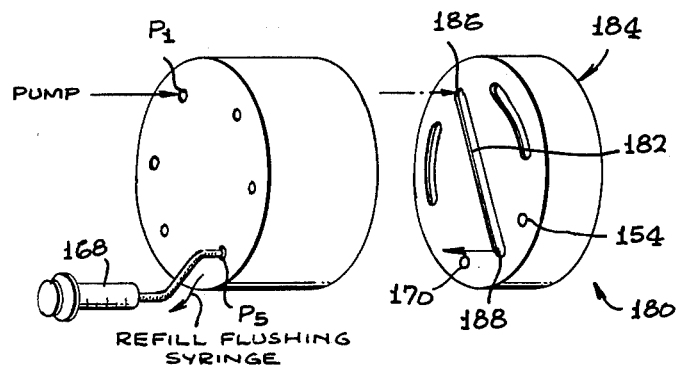

SAMPLE INJECTOR

BACKGROUND OF THE INVENTION

In the practice of liquid chromatography and other analytical methods involving flowing liquid streams, it is a common requirement to analyze samples which are available only in quantities less than one milliliter in volume. Furthermore, the columns employed for the analyses often require injection of small sample volumes, typically one to fifty microliters, in order to operate efficiently. It has become common practice to use sample injection devices which accept variable volumes of sample, transferred into the injector via an injector opening which accepts the needle of a micro syringe. The syringe serves to measure the volume of the introduced sample. The sample then resides in a chamber, often referred to as the sample loop, which is at atmospheric pressure. Upon subsequent actuation of the injector device, the sample is swept at a high pressure, of typically 100 to 10,000 psi, from the chamber and into the column by the flow of mobile phase from the pump.

One type of prior art injector device has a needle-receiving passage from which the syringe is withdrawn subsequent to the transfer of sample into the chamber, and which must be plugged prior to the actuation of the injector. The plug prevents loss of high pressure fluid from the port. Such devices are described in U.S. Pat. Nos. 3,916,692 by Abrahams et al and 3,961,534 by Gundelfinger. One advantage of such devices is that all of the sample transferred by the syringe is subsequently injected into the column, so there is no sample loss. This is beneficial because the syringe calibration marks on a conventional syringe provide an accurate indication of the volume actually injected into the column. Other advantages are that there is no waste of the sample, which is sometimes valuable and in limited supply, and there is no left over sample in the injector which could cause cross-contamination with the next sample to be injected. However, such injector devices have the disadvantage of requiring the needle passage to be plugged after syringe removal and prior to actuation. Removing the syringe needle and inserting the plug can lead to volumetric errors, since the sample chamber experiences the exiting and entering of the needle and plug probes. Furthermore, the entire process is somewhat complicated and tedious.

A second type of prior art injector device, that can be utilized without withdrawing the syringe or plugging the passage, is described in U.S. Pat. Nos. 4,022,005 by Ramin et al and 4,068,528 by Gundelfinger. However, such devices have the disadvantage that some of the sample transferred from the syringe, remains in the flow passage which connects the syringe needle to the sample chamber. As a consequence, some sample is wasted, and the left over sample can be a source of cross-contamination between samples. Such cross-contamination can be avoided by extensively flushing the connecting passage with a pure solvent between every injection, but this is inconvenient as it requires a second syringe to be inserted into the needle port. Another disadvantage is that the calibrations on a standard syringe do not accurately indicate the volume of sample injected into the column, since no account is taken of the trapped sample portion.. The user can factor in this error, or use a special syringe having calibrations offset to account for sample loss, but neither of these is as convenient as using a standard syringe and simple calculations.

An object of this invention is to provide an injector device which is easy to use, avoids wastage of sample, avoids cross-contamination of samples, and accurately delivers a sample to a chromatographic column in accordance with standard syringe calibrations.

SUMMARY OF THE INVENTION

In accordance with one embodiment of the present invention, a relatively simple and easily operated sample injector device is provided, which avoids the entrappment of the sample. The device includes stator and rotor elements with axially-facing adjacent surfaces, with one of the elements having a needle opening or passage for receiving a syringe needle, and with the other element having a port that can be aligned with the needle passage to receive the sample transferred through the needle. The needle passage extends parallel to, but offset from, the axis of rotation of the rotor. The tip of the syringe needle is ground flat and perpendicular to its axis. When the needle is fully inserted into the needle passage of the rotor element, the tip is in contact with the flat face of the stator element so that there is no connecting volume between the tip of the syringe needle and the aligned stator element port. The entire volume discharged by the syringe is then transferred to the sample loop via this port.

The novel features of the invention are set forth with particularity in the appended claims. The invention will be best understood from the following description when read in conjunction with the accompanying drawings.

BRIEF DESCRIPTION OF THE DRAWINGS

FIG. 10 is a partial sectional view of a sample injector constructed in accordance with another embodiment of the invention.

FIG. 11 is a partial sectional view of a sample injector device constructed in accordance with another embodiment of the invention.

FIG. 12 is a simplified exploded perspective view of the device of FIG. 11, shown in a load configuration, and after the sample has been loaded into the sample loop.

FIG. 13 is a view similar to FIG. 12, but showing the device after it has been turned to an inject configuration, and showing the device operated in a flush mode to prevent cross contamination after syringe needle removal.

FIG. 14 is a simplified exploded perspective view of a sample injector constructed in accordance with another embodiment of the invention.

DESCRIPTION OF THE PREFERRED EMBODIMENTS

Figure 1:
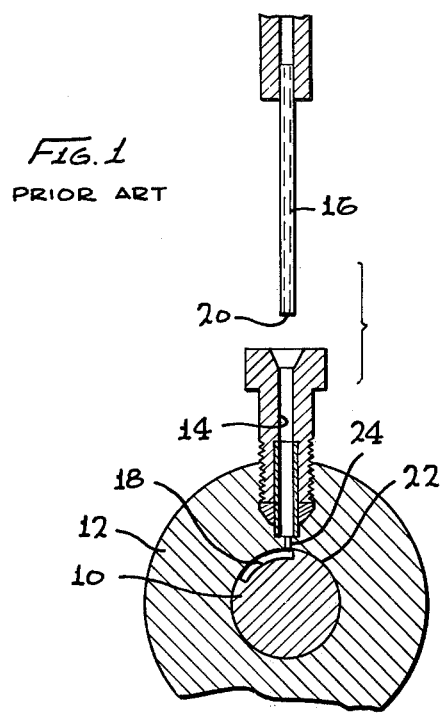
FIG. 1 is a partial sectional view of a prior art sample injector.
Figure 2:
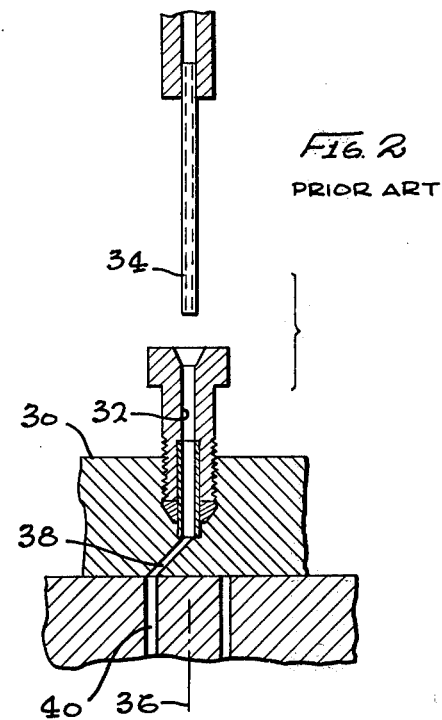
FIG. 2 is a partial sectional view of another prior art sample injector.

FIG. 1 illustrates one prior art sample injector, which includes a rotor 10 that lies within a cylindrical stator 12 that has a hole 14 for receiving the needle 16 of a syringe. When the needle is inserted into the hole to transfer fluid into a passage 18, the tip 20 of the needle lies behind the rotor-stator interface 22. Accordingly, when the rotor 10 is turned to pump the sample out of the passage 18, some of the sample will lie in a connecting passage 24 at the end of the needle-receiving hole. FIG. 2 illustrates another prior art sample injector, which includes a rotor 30 having a needle receiving hole portion 32 for receiving a needle 34. The hole portion 32 lies along the axis of rotation 36 of the rotor, and another hole portion 38 extending in a largely radial direction is provided to carry the sample to a stator port 40 spaced from the axis 36. The hole portion 38 extends largely radially to enable disconnection thereof from the stator port 40 when the rotor turns. However, the hole portion 38 holds a portion of the sample which is not utilized and which is therefore wasted. In both of the foregoing prior art sample injectors, some sample is wasted, and the sample remaining in the connecting passage is a source of cross contamination if it is not flushed out prior to the next injection.

Figure 3:
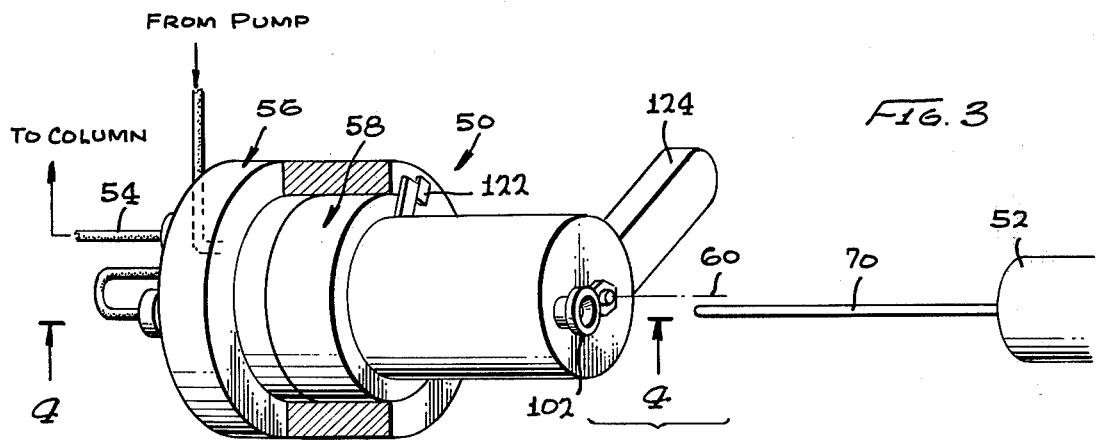
FIG. 3 is a partially sectional perspective view of a sample injector constructed in accordance with one embodiment of the present invention.
Figure 4:
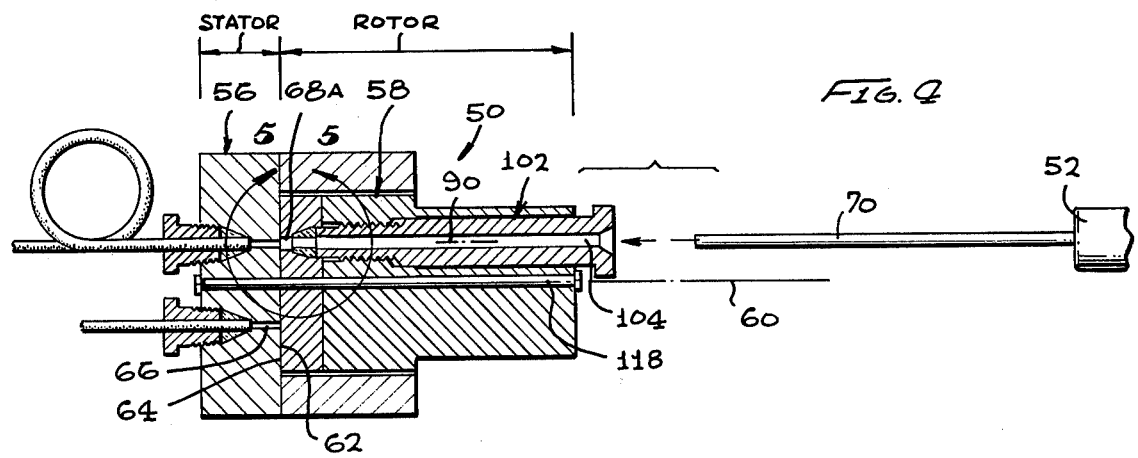
FIG. 4 is a view taken on the line 4—4 of FIG. 3.

FIG. 3 illustrates a sample injector of the present invention, which can receive a small sample from a micro syringe 52 and deliver the sample along a conduit 54 to a chromatographic column or other analytical device, without incurring any sample loss. The device includes a stator element or stator 56 and a rotor element or rotor 58 that rotates about an axis 60. As shown in FIG. 4, the stator and rotor have adjacent faces 62, 64 that each face in an axial direction, that is, each face extends normal to the axis of rotation 60. The stator has a group of six ports 66 that extend to the stator face 62. The rotor 58 has a frame with a group of openings or passages 68 spaced about the axis 60, that are open to the rotor face 64, so that they can communicate with the stator ports 66. One of the rotor passages 68A is a needle-receiving passage which is designed to receive the tube or needle 70 of the micro syringe. The other passages 68 in the rotor are arranged in interconnected pairs, and are utilized to interconnect selected pairs of stator ports 66. The rotor 58 can rotate, or pivot, about the axis 60 between two positions, to connect the needle-receiving passage 68A to different ports 66, and to utilize the other rotor passages 68 to interconnect different pairs of ports.

Figure 6:
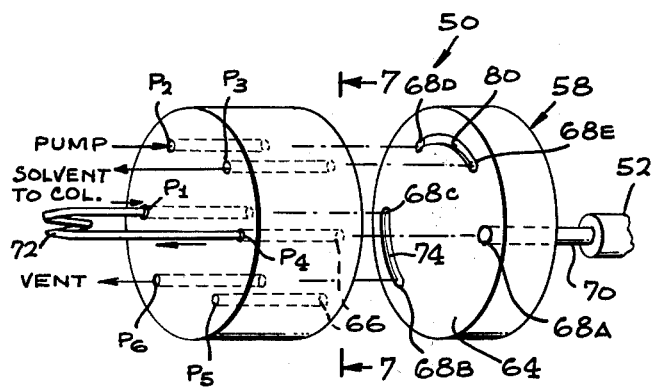
FIG. 6 is a simplified exploded view of the sample injector of FIG. 4, shown in a load configuration.

FIGS. 6–9, wherein the stator ports are labelled $P_1$ through $P_6$, show the injector device in two different positions. In FIG. 6 the sample injector device 50 is in a "load" configuration, wherein the rotor 58 is positioned so that the rotor passage 68A is aligned with stator port $P_4$. The solvent being pumped through the chromatographic system from the pump is connected to port $P_2$, and the column is connected to port $P_3$. The sample loop 72 is connected to ports $P_1$ and $P_4$. Ports $P_5$ and $P_6$ are connected to vent tubes and are always at atmospheric pressure. In practice, the sample loop 72 is made long enough to contain a volume of liquid greater than the largest sample volume to be introduced by the syringe. In operation, the sample loop contains solvent (from the pump) prior to the transfer of sample from the syringe into the loop.

Figure 7:
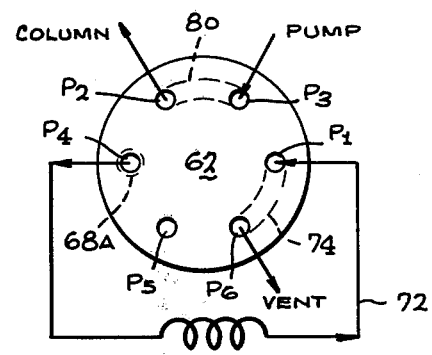
FIG. 7 is a view taken on the line 7—7 of FIG. 6.

With the device in the load configuration of FIGS. 6 and 7, the operator can insert the needle 70 of the microsyringe into the needle-receiving passage 68A, and then discharge the syringe to transfer the sample into the port $P_4$ which is aligned therewith. The sample flows through the port $P_4$ into the sample loop 72 connected therewith, and displaces an equal volume of solvent in the loop, through a vent port $P_6$ via the rotor passage 68C, rotor passage 74, and rotor passage 68B. Also, in this position of the device the pumped solvent flows directly to the column via the rotor passage 80 which joins rotor passages 68D and 68E. Thus, in the load position of the rotor 58 shown in FIG. 6, and also as indicated in FIG. 7, the sample can be transferred at atmospheric pressure into the sample loop 72 to prepare it for a subsequent high pressure injection into the chromatographic column.

Figure 8:
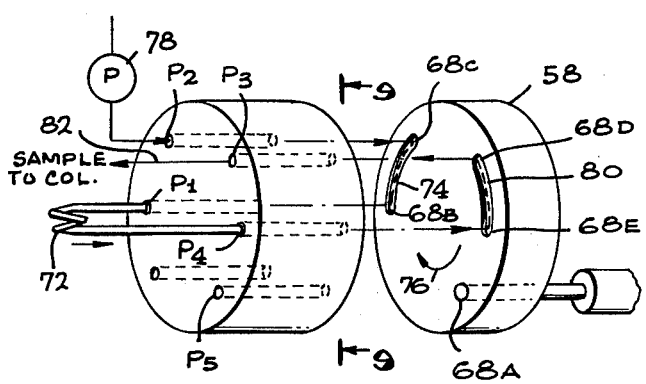
FIG. 8 is a simplified exploded perspective view of the device of FIG. 6, but shown in an inject configuration.
Figure 9:
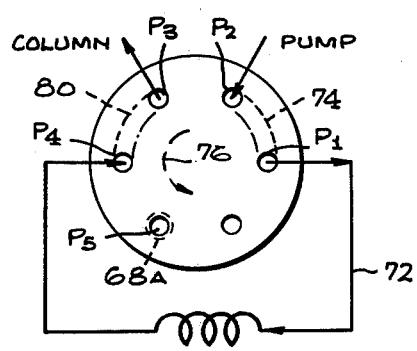
FIG. 9 is a view taken on the line 9—9 of FIG. 8.

FIGS. 8 and 9 illustrate the device 50 when it is in the "inject" position, wherein the rotor 58 has been turned in the direction of arrow 76 by an angle of 60°, so that the rotor passage 68A is now aligned with the stator port $P_5$. With the rotor in the inject position of FIG. 8, solvent pumped by a high pressure pump 78 can flow through port $P_2$, through rotor opening 68C and through passage 74 to rotor opening 68B, through port $P_1$, and through the sample loop 72. The sample lying in the loop 72 is thereby moved along by the solvent through the port $P_4$, through rotor opening 68E and a passage 80 to rotor opening 68D, and through port $P_3$, to flow the sample along a line 82 leading to the chromatographic column. Thus, while the sample loop 72 was initially filled with the sample at atmospheric pressure, the sample now can be pumped into the column under a high pressure (such as up to 10,000 psi) applied by the pump 78. All portions of the sample lying in the sample loop 72 and in the port $P_4$ will be pumped to the column.

Figure 5:
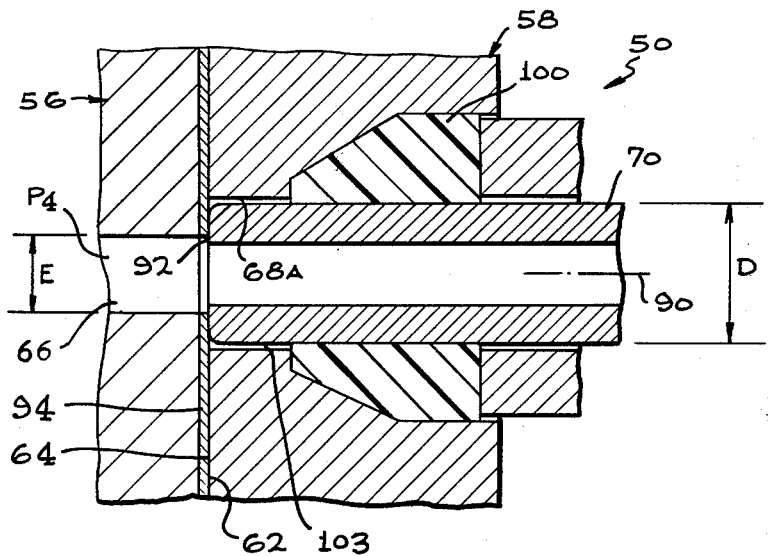
FIG. 5 is an enlarged view of the region 5—5 of FIG. 4.

Referring to FIGS. 4 and 5, which detail of the injector opening, the rotor includes a guide tube 102 for receiving the syringe needle 70. The needle is inserted into an opening 104 in the guide tube 102, passes through a seal 100, passes through the end of the rotor passage 68A, and abuts the flat face 62 of the stator. The seal is made of relatively easily compressible plastic such as polytetrafluroethylene and is compressed sufficiently by screwing in the guide tube 102 so that the seal hole squeezes tightly around the syringe needle to form a liquid-tight seal. In practice, the rotor passage 68A and the hole in the seal 100 are filled with solvent before inserting the syringe needle. When the needle is inserted, it is therefore surrounded by solvent and the seal effectively traps the solvent in the clearance space 103 surrounding the end of the needle, in the portion of the rotor passage 68A lying between the seal 100 and the stator face 62. Accordingly, any tendency for the sample that is discharged from the syringe to leak back out through the needle guide is prevented. The parallel flat face contact between the needle tip 92 and stator face 62 is precise enough to limit diffusion of sample liquid away from port $P_4$, to a negligible amount.

A major novelty of the present invention concerns the discovery that the flat syringe needle tip 92 can be pushed in to abut the stator face 62, and can be left there while the rotor 58 is turned so that face of tip 92 slides along the stator face 62.

FIG. 5 shows that the diameter of the stator port 66 is smaller than the outer diameter of the needle, preventing the needle from entering the port. Since the sliding action of the needle tip 92 against the stator face 62 can cause wear, the stator should be made of a material that is substantially harder than the needle. FIG. 5 shows a thin layer 94 which forms a hard surface on the stator face. Hard surface coatings of ceramic materials are commonly available for this purpose. The area contact between the flat tip of the needle which lies in a plane parallel to the flat stator face, minimizes the possibility of scratching a groove in the stator face during turning of the rotor by wear or microscopic chipping and crumbling. The rotor is rotatably mounted on a shaft 118 (FIG. 3) and can be turned by turning a handle 124.

Figure 9A:
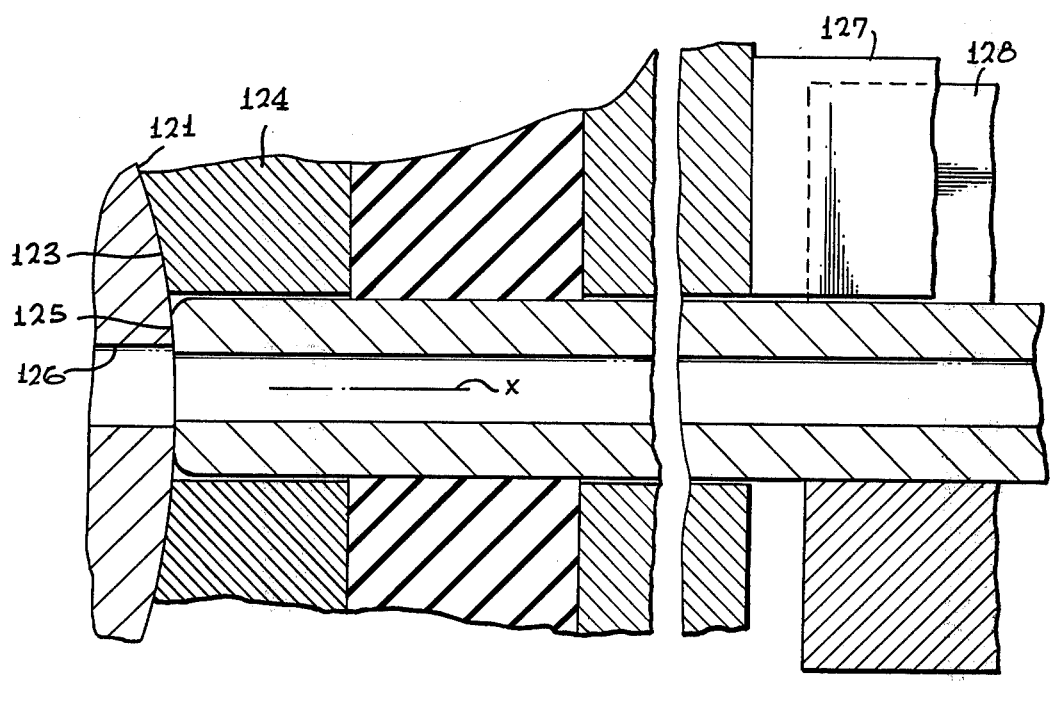
FIG. 9A is a partial sectional view of another sample injector.

The combination of a flat stator face 62 (FIG. 5) and a flat needle tip 92 that lies flush thereagainst, enables a fluid tight seal to be formed between the internal passage of the needle and the stator port 66. When a moderate force is applied to the needle, the sample will not leak into the clearance space 103 around the needle end, even if the seal 100 is not present, and this fluid-tight sealing against the needle tip will be maintained during pivoting of the rotor. In that case, the Teflon seal 100 that seals to the outside of the needle, serves as a backup seal. It is also possible to utilize a cylindrical rotor element, as indicated at 121 in FIG. 9A, which rotates within the mating cylindrical hole 123 in a stator element 124, and to utilize a needle with a mating cylindrical tip 125, that is held in contact with the rotor face before fluid transfer and during subsequent rotor pivoting. To assure contact of the needle tip at substantially 360° about the end of the rotor port 126, which is of circular cross section at its end, it is necessary to hold the needle at a predetermined rotational position about the needle axis X. This can be accomplished by providing a key 127 on the stator that receives a slot 128 on the body of the syringe. Of course, the needle can be allowed to be installed at an orientation rotated 180° from the one shown. This arrangement provides a 360° seal between the needle tip and rotor port, and also provides area contact of the needle face with the rotor surface to minimize wear or chipping of the rotor surface. It may be noted that it is possible to utilize a spherical outer surface in the rotor around the port 126 therein, to achieve 360° sealing contact around the port, although there would not be area contact with the needle and a spherical surface is more expensive to form. Area contact with a spherical element surface can be achieved by grinding the needle tip to a matching spherical form, but this is also more expensive.

Where somewhat more manipulation of the injection tube 70 than required in the device of FIG. 4 is acceptable, a device of the type shown at 130 in FIG. 10 can be utilized to inject a sample without entrapment and loss of sample. The device of FIG. 10 is utilized by inserting the syringe needle 70A through a rotor passage 132 of a rotor 134, until the tip 136 of the needle passes across the stator face 138 and lies in the aligned stator port 140. A stop 142 limits the depth of insertion of the needle until the stop abuts a shoulder on the micro syringe. The micro syringe 52 A is then operated to transfer the sample into the port 140 and into a sample loop 144 connected thereto. The syringe is then withdrawn so that the needle tip 136 lies behind the stator face 138, and the rotor is then turned by 60° to couple the high pressure pump to the sample tube 144 and to connect the port 140 to a rotor passage that leads to the column in the manner described above for the device for FIGS. 1–9.

FIG. 11 illustrates a sample injection device which has the advantage of the device illustrated in FIG. 4 of not requiring further manipulation of the syringe once it has been inserted, but which is similar to the device of FIG. 10 in that the needle tip is not located at the rotor-stator interface in contact with the stator face. In the sample injection device 150 of FIG. 11, a flush channel 152 is provided which leads to the end portion of the needle passage 154 in which the needle 70B lies. A quantity of flushing fluid such as the same solvent that is used to later pump the sample into the chromatographic column, is flushed through the passage 152, around the end of the needle 70B which lies beyond the seal 156, and into the stator port 158, to flush all of the sample into the port 158 and into the sample loop 160 connected thereto. Only a small amount of flushing fluid is passed through the passage 152, so that only a small amount of solvent will lie in the sample loop 160. The flushing permits the tip 162 of the needle to lie behind the stator face 164 at all times, to avoid contact with the stator face, and yet prevent loss of the injected sample.

FIGS. 12–13 illustrate additional details of the flushing type sample injection device 150 of FIG. 11. FIG. 12 shows the rotor 166 in the "load" position, wherein the rotor needle passage 154 is aligned with the port 158, so that the sample can be transferred into the sample loop 160. Following operation of the micro syringe 52B to transfer the sample, a flushing syringe 168 is operated. The flushing syringe is connected to a port $P_5$ which is aligned with an opening 170 in the rotor that leads to the flushing pasage 152, so that operation of the flushing syringe causes the flushing fluid to flow through the passage 152 and flush out any sample remaining in the needle passage 154. After the sample has been loaded and the flushing syringe 168 operated, the rotor is turned 60° to the position shown in FIG. 13, wherein the port $P_4$ is connected to another rotor opening 172, to allow the pumping of the small amount of flushing fluid and sample lying in the loop 160, into the chromatographic column. In this inject position of the rotor, the needle passage 154 of the rotor becomes aligned with the port $P_5$ to which the flushing syringe 168 is connected.

FIG. 14 illustrates a modified flushable sample injection device 180 which is similar to the device 150 of FIGS. 11–13, except that it permits automatic refilling of the flushing syringe 168. This is accomplished by the use of a recharging passage 182 which is formed in the rotor. The ends 186, 188 of the recharging passage are located so that they are in line with the stator port $P_1$ and the flushing port $P_5$ for a brief time as the rotor 184 is being rotated between the load and inject positions of FIGS. 12 and 13 respectively. That is, it requires a 60° pivoting of the rotor 184 to move it between its load and inject positions, but the channel ends 186, 188 become aligned with the ports $P_1$, $P_5$ after only a 30° rotation from the load position, this 30° rotational position being shown in FIG. 14. In this intermediate position, solvent pumped into the stator port $P_1$, flows through the passage 184 and through the port $P_5$ to refill the flushing syringe 158. The rotor will lie in this intermediate position for only a short time, while it is being rotated between its load and inject positions, but this short period is sufficient to recharge the flushing syringe with the small volume of flushing solvent required. This device therefore assures that the flushing syringe 168 will always be filled with solvent, to eliminate the need for constant maintenance of the syringe.

Thus, the invention provides a sample injector device of the type which can receive a sample to be analyzed by transfer from a syringe at atmospheric pressure, and then inject the sample at high pressure into a chromatographic column or other analyzing instrument, which avoids the loss of any sample while enabling operation of the device in a relatively simple manner. This can be accomplished by utilizing rotor and stator elements having axially facing surfaces, so that the surfaces can be flat at least around the communicating holes therein, and by utilizing a needle-receiving opening that receives an injection needle so that the needle can be received up against the face of the other element and can remain thereat during turning of the rotor. The needle-receiving opening, which may be formed in the rotor, extends along a straight line that is parallel to the axis of rotation but which is radially offset therefrom. The orientation of the needle-receiving opening parallel to the axis permits a needle with a tip perpendicular to the axis of the needle, to lie in sealing contact with the flat face of the engaged element around the port therein, to prevent the leakage of sample into the clearance space around the end of the needle. This arrangement also provides area contact of the needle tip against the face of the other element such as the stator, and the needle can remain thereagainst while the rotor turns without scratching or chipping a groove in the face which the needle tip contacts during numerous operations of the device. The needle-receiving opening can be sealed against the outside of the needle by utilizing a seal of easily compressible material, and by providing a needle guide which is biased against the seal to axially compress it so that the seal then presses tightly against the injection tube, to provide a backup seal that avoids backward leakage of the sample. A backup seal of slippery material such as Teflon, avoids springing back when pressure on the syringe is released, so that such a backup seal can hold the needle flush against the element face even though the operator stops applying force. The backup seal can extend up to the element interface. Cylindrical rotor and stator elements cen be utilized, with a seal formed at the needle tip by utilizing a matching cylindrical needle tip surface and controlling the orientation of the needle about its axis, and it is also possible to utilize spherical surfaces. In another embodiment of the invention, the device is constructed so that the tip of the needle passes the rotor-stator interface, where it remains during atmospheric pressure transfer of sample from the syringe, and wherein the needle is withdrawn behind the rotor-stator interface before the rotor is turned. In still another embodiment of the invention, the tip of the needle can lie behind the rotor-stator interface, but a flushing passage is provided which leads to the end of the needle-receiving opening, to flush any remaining sample therein into the other element prior to the rotation of the rotor. It should be noted that sample transfer tubes other than those on syringes can be utilized, and the term needle is herein utilized to refer to any small diameter tube. It also may be noted that the needle-receiving passage can be formed in a stator element instead of a rotor element.

Although particular embodiments of the invention have been described and illustrated herein, it is recognized that modifications and variations may readily occur to those skilled in the art, and consequently, it is intended that the claims be interpreted to cover such modifications and equivalents.

The embodiments of the invention in which an exclusive property or privilege is claimed are defined as follows:

1. A sample injector device for receiving a sample to be analyzed from an injector tube and transfering the sample to an analyzing instrument, comprising:
    a stator element;
    a rotor element rotatably mounted on said stator element about a predetermined axis, said elements having facewise adjacent faces;
    a first of said elements having a plurality of ports open to said face thereof;
    a second of said elements having a tube-receiving passage open to the face thereof to communicate with ports in said first element;
    said tube-receiving passage extending through said second element, along a straight line to the face thereof, so the face end portion of the tube-receiving passage can receive a straight injector tube with its tip lying at the interface of said elements, and said first element having a port with an end that is aligned with said tube-receiving passage and that is narrower than the face end of said tube-receiving passage, whereby the injector tube can lie flush against the face of the first element.

2. The device described in claim 1 including:
    an injection device having an injector tube of a length and diameter that fits through said tube-receiving passage against the face of said first element, said first element having a flat face and said tube tip having a flat surface that can lie flush with said first element face against the area thereof surrounding one of said ports therein.

3. The device described in claim 1 including:
    an injection device having an injector tube of a length and diameter that fits through said tube-receiving passage against the face of said first element, said first element having a cylindrical face and said tube tip having a matching cylindrical surface that can lie flush with said first element face against the area thereof surrounding one of said ports therein, in a predetermined rotational position of the tube, and said injection device including means that can hold it with said tube in said rotational position.

4. The device described in claim 1 wherein:
    said stator surrounds said rotor and said stator and rotor have adjacent face portions of matching spherical shape, whereby to enable sealing of an injection tube tip to the entire rim of the rotor port it lies against.

5. The device described in claim 1 wherein:
    said first element face is flat around said ports, and said tube-receiving passage extends perpendicular to said faces;
    said second element has at least two additional passages spaced about the axis of rotation of the rotor, and that are interconnected;
    said first element has a plurality of ports spaced about said axis of rotation; and
    said line along which said tube-receiving passage extends, extends parallel to the axis of rotation of the rotor but is radially spaced therefrom.

6. The device described in claim 1 including:
    a seal disposed along said tube-receiving passage and sealable against the outside of the injector tube, to prevent the backward flow of sample fluid around said tube.

7. A sample injector device for receiving a sample to be analyzed from an injector tube and transferring the sample to an analyzing instrument, comprising:
   a stator element;
   a rotor element rotatably mounted on said stator element about a predetermined axis, said elements having axially facing adjacent faces;
   a first of said elements having a plurality of ports open to said face thereof;
   a second of said elements having a plurality of passages, including a tube-receiving passage, said passages spaced about said axis and open to the face of said second element to communicate with ports in said first element, and said second element having at least one interconnect passage that connects a pair of said passages;
   said tube-receiving passage extending along said second element, along a straight line which is parallel to said axis of rotation but radially spaced therefrom, so the face end portion of the tube-receiving passage can closely receive a straight injector tube with its tip lying at the interface of said elements, and said first element having a port with an end that is aligned with said tube-receiving passage and that is narrower than the face end of said tube-receiving passage, whereby the injector tube can lie flush against the face of the first element.

8. The device described in claim 7 including:
   a fluid injector which includes a narrow tube of a diameter that fits closely within the tube-receiving passage at the end thereof which lies adjacent to said first element, said tube having a tip face lying on a plane which is perpendicular to the axis of the tube, to lie flush with the face of the first element.

9. The device described in claim 7 including:
   a seal disposed about said tube-receiving passage and having a hole which closely receives a tube whose end is closely received in said tube-receiving passage, to form a substantially fluid-tight seal around the tube.

10. The device described in claim 7 wherein:
   said rotor is rotatable between first and second positions wherein first and second of said ports are alternately aligned with said tube-receiving passage, said first and second ports being of substantially circular cross section at said first element face and being of smaller diameter thereat than the tube-receiving passage, to prevent the entrance into said ports of an injector tube which closely fits through the tube-receiving passage.

11. The device described in claim 10 including:
   a syringe which includes a needle with a diameter that closely fits in the end portion of the tube-receiving passage that lies adjacent to said second element face, the end of said tube having a larger outside diameter than either of said first and second ports.

12. In a sample injector device which includes stator and rotor elements wherein a first element has ports and the other element has passages including a needle-receiving passage for receiving a syringe needle with a substantially flat tip, the improvement wherein:
   said elements have facewise adjacent faces which are flat and lie in planes normal to the axis of rotation of the rotor;
   said needle-receiving passage is radially spaced a predetermined distance from said axis of rotation;
   a pair of said ports are radially spaced by said distance from the axis to alternately lie aligned with said needle-receiving passage when said rotor is turned; and
   said needle-receiving passage extends along a line parallel to but spaced from said axis of rotation, so that the needle can lie in the needle-receiving passage with the needle tip flush with the element faces; and
   the element which forms said needle-receiving passage includes a seal that can form a fluid-tight seal around a needle whose tip lies flush with the element faces.

13. The improvement described in claim 12 including:
   a syringe which has a needle of a diameter that closely fits in the needle-receiving passage portion that lies adjacent to said element faces; and
   at least one of said ports of said pair of ports has a diameter, at said element faces, which is smaller than the needle tip outer diameter.

14. In a sample injector device which includes stator and rotor elements, wherein one of said elements has ports and the other element has passages including a tube-receiving passage for receiving an injector tube, and wherein said elements have adjacent faces to which said ports and passages extend, the improvement wherein:
   said tube-receiving passage lies in a first of said elements and extends along a straight line through said first element, to permit the reception of an injector tube through the entire length of the passage; and
   a second of said elements which forms said ports, includes first and second ports which can be alternately aligned with said tube-receiving passage, said first port having a diameter at least about the same diameter as the tube-receiving passage end nearest to the second element face, to permit the reception of an injector tube through the tube-receiving passage and into said first port.

15. The improvement described in claim 14 including:
   a sample injector which includes an injector tube of a length and diameter to pass through said tube-receiving passage and into said first port.

16. In a sample injector device which includes stator and rotor elements, wherein one of the elements has ports and the other has passages including a tube-receiving passage for receiving an injector tube, and wherein said elements have adjacent faces to which said ports and passages extend so at least some ports and passages can be aligned, the improvement wherein:
   said tube-receiving passage lies in a first of said elements and extends along a straight line through at least most of said first element, to permit the reception of an injector tube to a position near the face of the first element;
   said first element includes a flush passage intersecting said tube-receiving passage at a location spaced from the first element face; and including
   means for applying a flushing fluid through said flush passage into said tube-receiving passage, to flush liquid lying in said tube-receiving passage into a port aligned with said tube-receiving passage.

17. The improvement described in claim 16 including:
   an injector with an injector tube of predetermined length; and stop means on said first element for limiting the depth of insertion of said tube into said opening to a depth at which said injector tube lies beyond the intersection of the flush passage with the tube-receiving passage, but behind the face end of the tube-receiving opening.

18. The improvement described in claim 16 wherein:
said flush passage extends to the face of said first element at a location spaced from said tube-receiving passage; and
said means for applying a flushing fluid includes a refillable flushing syringe means for applying flushing fluid, said syringe means connected to a first of said ports which is aligned with said flush passage location.

19. The improvement described in claim 18 including:
a pressured flushing fluid supply connected to a second of said ports of said second element at a location spaced from the rotor-stator interface; and
walls forming a recharging passage in said first element, said recharging passage having ends respectively aligned with said first and second ports when said rotor is turned to a predetermined position, to then carry pressured flushing fluid from the flushing fluid supply to the flushing syringe means to recharge the syringe means.

20. A method for injecting a fluid sample into an analyzing instrument, comprising:
inserting a syringe needle into a needle-receiving passage of a first element which has a surface adjacent to that of a second element which has a port aligned with the needle-receiving passage, wherein one of said elements is a stator and the other is a rotor, said inserting continuing until the tip of the needle abuts the second element surface;
operating the syringe to transfer a sample from the tip thereof directly into said second element port which is aligned therewith; and
turning the rotor while maintaining the needle tip in abutment with said second element surface, to align said port with another second element passage that is coupled to the instrument, and pumping fluid through said port and said another passage to the instrument.

21. The method described in claim 20 wherein:
said element surfaces are flat, said needle has a flat tip lying in a plane perpendicular to the axis of the needle, and the needle is inserted along a line perpendicular to said element surfaces.

22. The method described in claim 20 wherein:
said element surfaces are of matching cylindrical shape, and said needle has a matching cylindrical tip surface and is held in a rotational position with respect to the needle axis at which the tip surface is curved about the same axis as the element surfaces.

23. A method for injecting a fluid sample into an analyzing instrument, comprising:
inserting a syringe needle with a flat tip into a needle-receiving passage of a rotor which has a flat surface adjacent to a flat surface of a stator, along a line perpendicular to said surfaces until the tip of the needle abuts the stator surface;
operating the syringe to transfer a sample from the tip thereof directly into a stator port aligned therewith; and
turning the rotor while maintaining the needle tip in abutment with said stator surface, to align the stator port with a second rotor passage that is coupled to the instrument, and pumping fluid through said port and second rotor passage to the instrument.

* * * * *